United States Patent
Gran et al.

(10) Patent No.: US 11,559,281 B2
(45) Date of Patent: Jan. 24, 2023

(54) CMUT HEATLESS CODED ULTRASOUND IMAGING

(71) Applicant: B-K Medical Aps, Herlev (DK)

(72) Inventors: Fredrik Gran, Limhamn (SE); Ramin Moshavegh, Soborg (DK)

(73) Assignee: B-K MEDICAL, APS, Herlev (DK)

( * ) Notice: Subject to any disclaimer, the term of this patent is extended or adjusted under 35 U.S.C. 154(b) by 1534 days.

(21) Appl. No.: 15/702,050

(22) Filed: Sep. 12, 2017

(65) Prior Publication Data

US 2019/0076122 A1    Mar. 14, 2019

(51) Int. Cl.
*A61B 8/13* (2006.01)
*A61B 8/00* (2006.01)
(Continued)

(52) U.S. Cl.
CPC .............. *A61B 8/4483* (2013.01); *A61B 8/12* (2013.01); *G01S 7/5202* (2013.01); *G01S 7/52026* (2013.01); *G01S 15/8915* (2013.01); *G01S 15/8925* (2013.01); *G01S 15/8959* (2013.01); *G10K 11/346* (2013.01);
(Continued)

(58) Field of Classification Search
CPC ....... A61B 8/12; A61B 8/4483; G01S 7/5202; G01S 7/52026; G01S 7/52025; G01S 7/52079; G01S 15/8915; G01S 15/8959; G01S 15/8927; G01S 15/8925; G10K 11/346; G10K 11/348
See application file for complete search history.

(56) References Cited

U.S. PATENT DOCUMENTS

| 8,465,431 B2 | 6/2013 | Daft et al. |
| 2005/0004468 A1* | 1/2005 | Abend ................ G01S 7/5206 600/453 |

(Continued)

OTHER PUBLICATIONS

Caliano, et al., Capacitive Micromachined Ultrasonic Transducer (cMUT) made by a Novel "Reverse Fabrication Process", 2005 IEEE Ultrasonics Symposium pp. 479-482.
(Continued)

*Primary Examiner* — Patricia J Park
(74) *Attorney, Agent, or Firm* — Daugherty & Del Zoppo Co. LPA (57) ABSTRACT

An imaging system includes transmit circuitry, a transducer array with an array of capacitive micromachined ultrasonic transducer elements, a beamformer, a decoder and a display.
(Continued)

The transmit circuitry includes a signal generator and at least one excitation coding scheme. The transmit circuitry combines an excitation signal generated by the signal generator with an excitation coding scheme of the at least one excitation coding scheme, generating a coded excitation signal. The array of transducer elements is excited with the coded excitation signal to emit ultrasound signals. The coding scheme does not introduce heating on the capacitive micromachined ultrasonic transducer elements. The array of ultrasonic transducer elements receives echo signals produced in response to the ultrasound signals interacting with structure and generates electrical signals indicative thereof. The beamformer beamforms the electrical signals, the decoder removes the coding from the beamformed signals, and the display displays an image with the decoded signals.

20 Claims, 5 Drawing Sheets

(51) Int. Cl.
  *A61B 8/12* (2006.01)
  *G10K 11/34* (2006.01)
  *G01S 15/89* (2006.01)
  *G01S 7/52* (2006.01)

(52) U.S. Cl.
  CPC ........ *G10K 11/348* (2013.01); *G01S 7/52025* (2013.01); *G01S 7/52079* (2013.01); *G01S 15/8927* (2013.01)

(56) References Cited

U.S. PATENT DOCUMENTS

| | | | |
|---|---|---|---|
| 2013/0116561 A1* | 5/2013 | Rothberg | A61B 8/13 600/438 |
| 2014/0169136 A1* | 6/2014 | Booij | G01S 5/30 367/117 |
| 2016/0066881 A1* | 3/2016 | Li | A61B 8/12 600/443 |

OTHER PUBLICATIONS

Daft, et al., cMUTs and electronics for 2D and 3D imaging: Monolithic integration, in-handle chip sets and system implications, 2005 IEEE Ultrasonics Symposium pp. 463-474.

Gran, et al., Coded Ultrasound for Blood Flow Estimation Using Subband Processing, 2008 IEEE vol. 55, No. 10, Oct. 2008.

Kim, et al., An Experimental Study on Coded Excitation in CMUT Arrays to Utilize Simultaneous Transmisson Multiple-Zone Focusing Method with Frequency Divided Sub-band Chirps, 2013 Joint UFFC, EETF and PFM Symposium, pp. 1428-1431.

Lei, et al., Output Pressure and Harmonic Characteristics of a CMUT as Function of Bias and Excitation Voltage, 2015 IEEE International Ultrasonics Symposium Proceedings, 2015.

Oralkan, et al. Capacitive Micromachined Ultrasonic Transducers: Next-Generation Arrays for Acoustic Imaging?, IEEE Transactions on Ultrasonics, Ferroelectrics and Frequency Control, vol. 49, No. 11, Nov. 2002.

Tekes, et al., Improved FL-IVUS Imaging with Low Voltage Single-Chip CMUT-on-CMOS Array Using Temporally Coded Excitation, 2014 IEEE International Ultrasonics Symposium Proceedings, pp. 1308-1311, 2014.

* cited by examiner

CMUT HEATLESS CODED ULTRASOUND IMAGING

TECHNICAL FIELD

The following generally relates to ultrasound imaging with an ultrasound transducer array with a capacitive micromachined ultrasonic transducer (CMUT), and is described with particular application to CMUT heatless coded ultrasound imaging.

BACKGROUND

Ultrasound imaging has been used to determine information about the interior characteristics of an object or a subject. Generally, an ultrasound imaging system includes a transducer array and components for at least generating and transmitting ultrasound waves, receiving echoes or reflected waves, and generating ultrasound images thereon. The arrays have included a piezoelectric (PZT) or a capacitive micromachined ultrasonic transducer (CMUT) element. CMUT arrays, relative to PZT arrays, have greater design flexibility, are more compatibility with complementary metal-oxide-semiconductor (CMOS) technology, and are easier to fabricate, resulting in a possible lowering of transducer cost. CMUT arrays also have low mechanical impedance, which results in a large immersion bandwidth and therefore high axial resolution. However, as a consequence of the low mechanical impedance, the output pressure is lower compared to PZT arrays, and thus, unfortunately, CMUT arrays are less suited for deep imaging than PZT arrays. A thickness of the moveable membrane of a CMUT can be increased so that a larger voltage can be applied to increase the output pressure and imaging depth. However, this reduces the bandwidth and axial resolution, degrading image quality and possibly diagnostic value.

SUMMARY

Aspects of the application address the above matters, and others.

In one aspect, an imaging system includes transmit circuitry, a transducer array with an array of capacitive micromachined ultrasonic transducer elements, a beamformer, a decoder and a display. The transmit circuitry includes a signal generator and at least one excitation coding scheme. The transmit circuitry combines an excitation signal generated by the signal generator with an excitation coding scheme of the at least one excitation coding scheme, generating a coded excitation signal. The array of capacitive micromachined ultrasonic transducer elements is excited with the coded excitation signal to emit ultrasound signals. The coding scheme does not introduce heating on the capacitive micromachined ultrasonic transducer elements. The array of capacitive micromachined ultrasonic transducer elements receives echo signals produced in response to the ultrasound signals interacting with structure and generates electrical signals indicative thereof. The beamformer beamforms the electrical signals, the decoder removes the coding from the beamformed signals, and the display that displays an image with the decoded signals.

In another aspect, a method includes generating a coded excitation signal. The method further includes exciting a transducer array to emit an ultrasound signal with the coded excitation signal. The transducer array includes an array of capacitive micromachined ultrasonic transducer elements. A coding scheme of the coded excitation signal does not introduce heating on the capacitive micromachined ultrasonic transducer elements. The method further includes receiving signals indicative of echoes received by the transducer array. The echoes are produce in response to the ultrasound signal interacting with structure. The method further includes beamforming the signals. The method further includes decoding the beamformed signals. The method further includes visually presenting an image with the decoded signals.

In another aspect, a computer readable medium is encoded with computer executable instructions which when executed by a processor cause the processor to: generate a coded excitation signal with a heatless coding scheme, excite a transducer array to emit an ultrasound signal with the coded excitation signal, wherein the transducer array includes an array of capacitive micromachined ultrasonic transducer elements beamform echo signals received by the transducer array, extract a true signal from the beamformed signals, and display an image with the true signal.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements and in which.

DETAILED DESCRIPTION

Figure 1:
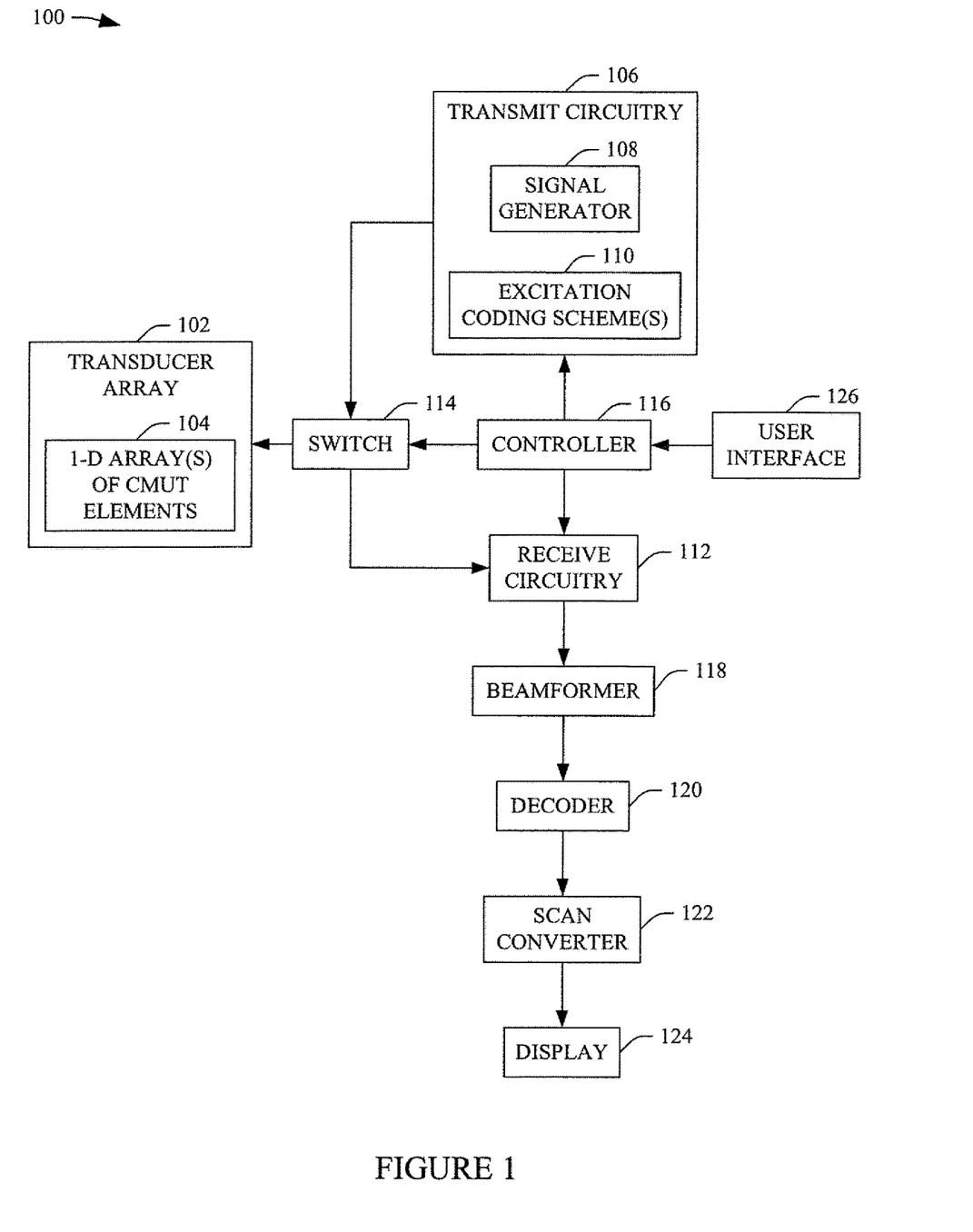
FIG. 1 schematically illustrates an example ultrasound imaging system configured for CMUT coded imaging.

FIG. 1 schematically illustrates an example imaging system 100, such as an ultrasound imaging system.

A transducer array 102 includes at least one one-dimensional (1-D) array of capacitive micromachined ultrasonic transducer (CMUT) elements 104, including a two-dimensional (2-D) matrix array and a 2-D array configured for row-column addressing. An example 1-D array of CMUT elements 104 includes a 16, 32, 64, 128, 192, 256, or other number of CMUT elements. The at least one 1-D array of CMUT elements 104 is configured to transmit ultrasound signals when in transmit mode. The at least one 1-D array of CMUT elements 104 is also configured to receive echoes and generate electrical signals indicative thereof when in receive mode. Generally, the echoes or reflected waves are generated in response to the transmitted ultrasound signals interacting with structure.

Transmit circuitry 106 generates an excitation signal that excites a predetermined set of the at least one 1-D array of CMUT elements 104 to transmit the ultrasound signals. The illustrated transmit circuitry 106 includes a signal generator 108 and an excitation coding scheme(s) 110. As described in greater detail below, in one instance, the signal generator 108 generates a sinusoidal and/or other signal, and the excitation signal is a combination of the sinusoidal signal and the excitation coding scheme, referred to herein as a coded excitation signal. A suitable excitation coding scheme is any binary coding scheme that does not include zeros (0's), e.g., just positive ones (1's) and negative ones (−1's), etc. In another instance, the excitation signal is just the sinusoidal signal, e.g., when the coding is not utilized.

Receive circuitry 112 receives the electrical signals with a predetermined set of the at least one 1-D array of CMUT elements 104.

A switch 114 switches between the transmit circuitry 106 and the receive circuitry 112, depending on whether the transducer array 102 is being operated in transmit or receive mode. In transmit mode, the switch 114 electrically connects the transmit circuitry 106 with the at least one 1-D array of CMUT elements 104. In receive mode, the switch 114 electrically connects the receive circuitry 112 with the at least one 1-D array of CMUT elements 104.

A controller 116 controls the transmit circuitry 106, the receive circuitry 112, and the switch 114 based on whether the at least one 1-D array of CMUT elements 104 is transmitting or receiving, etc. As described in greater detail below, in one embodiment, such control includes controlling the transmit circuitry 106 to transmit a coded excitation signal for CMUT coding imaging.

A beamformer 118 processes the electrical signals, for example, by applying time delays and weights and summing, and/or otherwise processing the electrical signals.

A decoder 120 removes the coding from the beamformed signals when the coded excitation signal is utilized for CMUT coding imaging. As described in greater detail below, in one instance, this first includes extracting the signal from the coded data. When the excitation signal is just the sinusoidal signal, the decoder 120 can be operated as a pass through or by passed. In a variation, the decoder 120 is configured to decode the individual signals (e.g., 192) output by the receive circuitry 112 and the beamformer 118 beamforms the decoded signals from the decoder 120.

In one instance, the coding/decoding approach described herein compensates for a low output pressure of the CMUT elements, increasing the signal-to-noise ratio (SNR) and penetration depth while maintaining bandwidth, without significant heating of the at least one 1-D array of CMUT elements 104. This approach also enables adaptive and/or frequency multi-band imaging. This allows for wide temporal bandwidth, good axial resolution, and both low and high frequency imaging with the same transducer array 102, rendering the transducer array 102 well-suited for multi-imaging applications (e.g., shallow and deep).

A scan converter 122 scan converts the beamformed and decoded signal, converting this data (e.g., an image) into the coordinate system of a display 124, which visually displays the data.

A user interface 126 includes include one or more input devices (e.g., a button, a knob, a slider, a touch pad, etc.) and/or one or more output devices (e.g., a display screen, lights, a speaker, etc.). A particular mode, scanning, and/or other function can be activated by one or more signals indicative of input from the user interface 126. For example, the user interface 126 can be used to select an acquisition protocol using an excitation coding scheme.

In one instance, the transducer array 102 is part of a probe and the components 106-126 are part of a console. Communication there between can be through a wired (e.g., a cable and electro-mechanical interfaces) and/or wireless communication channel. In this instance, the console can be similar to a portable computer such as a laptop, a notebook, etc., with additional hardware and/or software for ultrasound imaging. The console can be docked to a docketing station and used. Alternatively, the console can be part (fixed or removable) of a mobile or portable cart system with wheels, casters, rollers, or the like, which can be moved around.

In a variation, the display 124 may be separate from the console and connected thereto through a wired and/or wireless communication channel. Where the cart includes a docking interface, the laptop or notebook computer type console can be interfaced with the cart and used. An example of a cart system where the console can be selectively installed and removed is described in US publication 2011/0118562 A1, entitled "Portable ultrasound scanner," and filed on Nov. 17, 2009, which is incorporated herein in its entirety by reference.

Alternatively, the imaging system 100 is a hand-held ultrasound apparatus that houses and/or encloses the components 102-126, where the housing mechanically supports and/or shields the components within. In this instance, the transducer 102 and/or the display 124 may be part of the housing, being structurally integrated or part of a surface or end of the hand-held ultrasound apparatus. An example of a hand-held device is described in U.S. Pat. No. 7,699,776, entitled "Intuitive Ultrasonic Imaging System and Related Method Thereof," and filed on Mar. 6, 2003, which is incorporated herein in its entirety by reference.

As briefly discussed above, in one instance, the transmit circuitry 106 transmits a coded excitation signal, and the decoder 120 extracts the signal from the beamformed signal. The following provides a non-limiting example.

Figure 2:
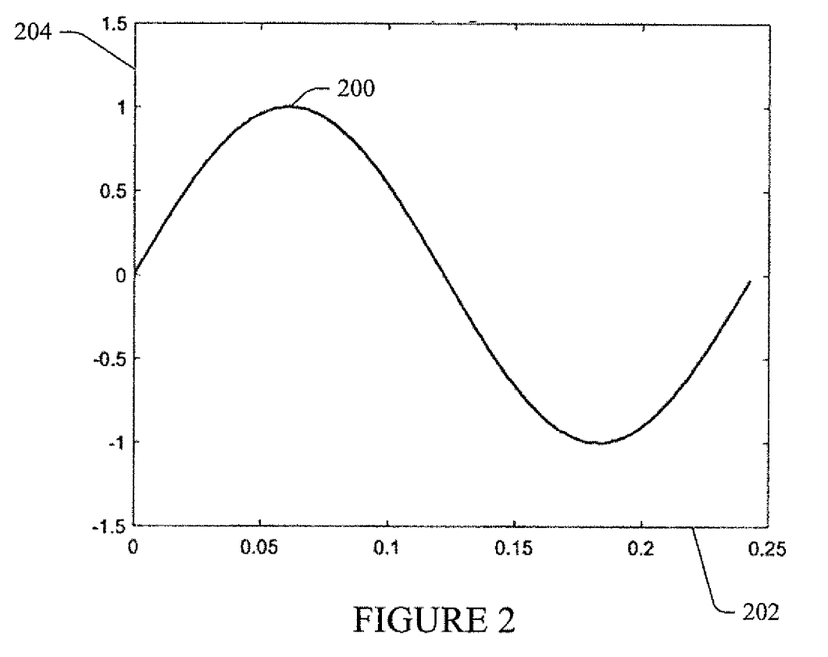
FIG. 2 schematically illustrates an example sinusoidal excitation signal.

FIG. 2 shows an example an example of a signal generated by the signal generator 108. In this example, the signal is a sinusoidal signal 200. Other signals are contemplated herein. A first (x) axis 202 represents time duration (e.g., in microseconds, μs), and a second (y) axis 204 represents a normalized amplitude. In this example, the sinusoidal signal 200 oscillates in a range from one (1) to negative one (−1) over a time duration of approximately 0.25 μs.

Figure 3:
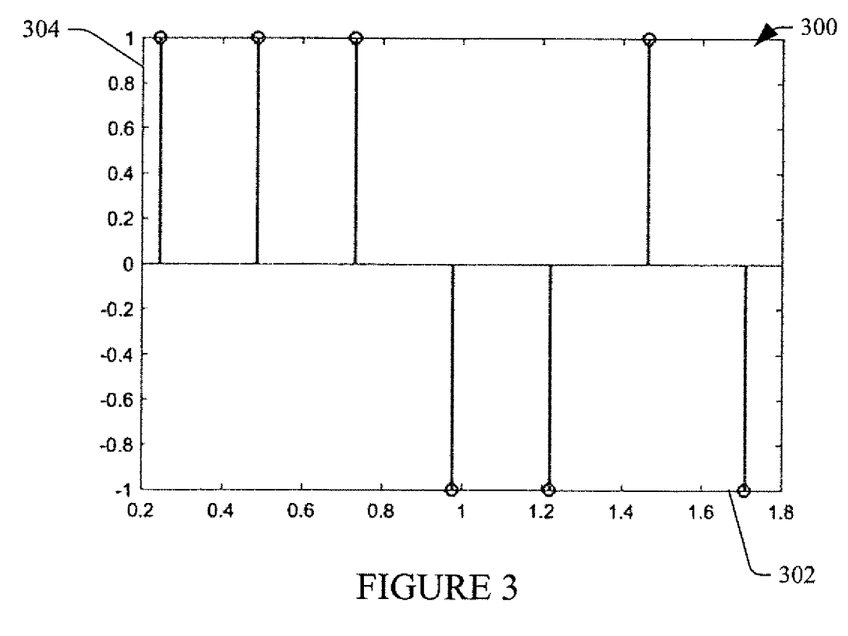
FIG. 3 schematically illustrates an example binary coding scheme that can be used for CMUT coded imaging.

FIG. 3 shows an example of an excitation coding scheme 300. In this example, the excitation coding scheme is the 7-bit Barker code +1 +1 +1 −1 −1 +1 −1. A first (x) axis 302 represents time duration (e.g., in μs), and a second (y) axis 304 represents a normalized amplitude. In this example, each bit of the excitation coding scheme 300 is either a one (1) or a negative one (−1).

A general N-bit Barker code c can be denoted as shown in EQUATION 1:

$$c = (c(0) c(1) \ldots c(N-1)), \qquad \text{EQUATION 1}$$

where N represents a total number of bits. From this, the 7-bit (N=7) Barker code c7 can be denoted as shown in EQUATION 2:

$$c7 = (1\ 1\ 1\ -1\ -1\ 1\ -1), \qquad \text{EQUATION 2}$$

To generate a coded excitation signal, the transmit circuitry 106 decreases a bit-rate of the code and then convolves the code with the sinusoidal signal. This can be achieved as shown in EQUATION 3:

$$s(n) = \sum_{l=0}^{N-1} c(l)p(n - l \cdot Tf_s),  \quad \text{EQUATION 3}$$

where s(n) represents the coded excitation signal, n represents a sample time, l is an index of the bits (0 to 6 where N=7), c(l) represents a code for the lth bit, p(n) represents the signal from the signal generator 108 at the sample time n, T represents a time duration between bits, and $f_s$ represents a sampling frequency.

Figure 4:
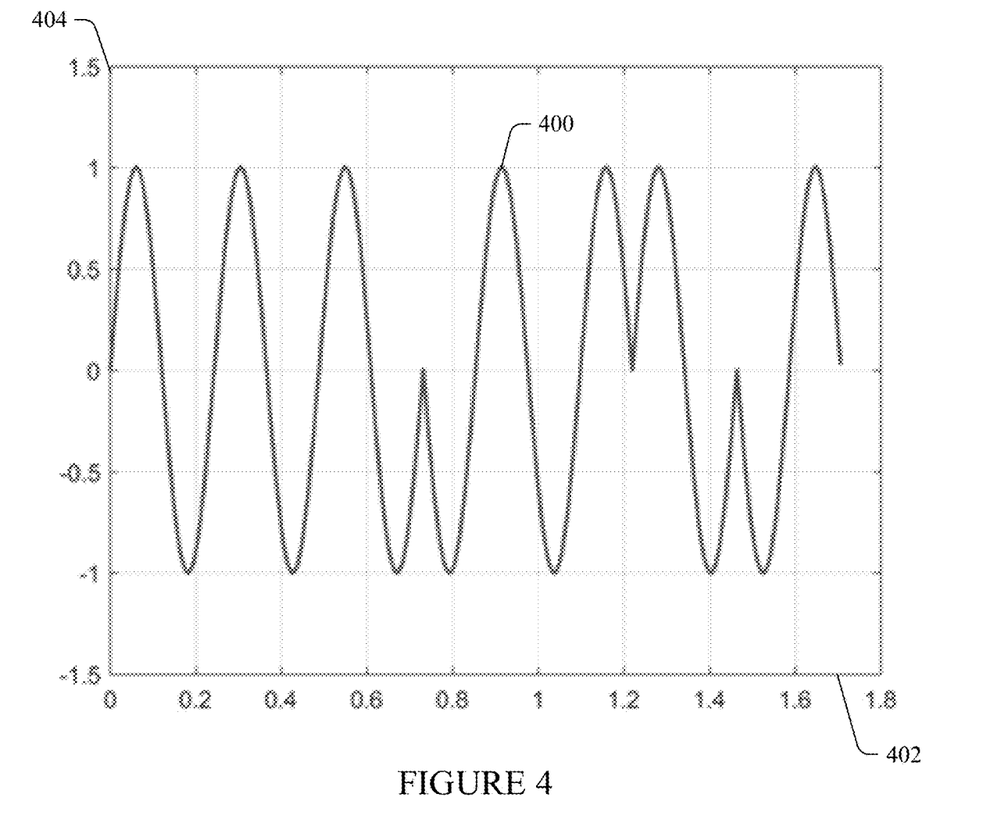
FIG. 4 schematically illustrates an example coded excitation signal for CMUT coded imaging.

FIG. 4 shows an example of a coded excitation signal 400 for the sinusoidal signal 200 in FIG. 2 and the 7-bit Barker code scheme 300 in FIG. 3. A first (x) axis 402 represents time duration (e.g., in µs), and a second (y) axis 404 represents a normalized amplitude. In this example, the coded excitation signal 400 oscillates in a range from positive one (+1) to negative one (−1). Some peaks oscillate between positive one (+1) and negative one (−1), while other peaks oscillate between negative one (−1) and zero (0) or positive one (+1) and zero (0), e.g., due to transition from positive to negative or negative to positive in the coding scheme 300.

The decoder 120, for code compression, applies an inverse filter. In this example, the decoder 120 employs a finite impulse response (FIR) filter which approximates an inverse filter of the code sequence utilized (the Barker code in this example). The following provides an example of such a filter.

A Fourier transform of the code is shown in EQUATION 4:

$$C(f) = \sum_{n=0}^{N-1} c(n)e^{-j2\pi(f/f_s)n}, \quad -\frac{f_s}{2} \le f \le \frac{f_s}{2}. \quad \text{EQUATION 4}$$

An inverse of the Fourier transform of EQUATION 4 is shown in EQUATION 5:

$$D(f) = \frac{1}{C(f)e^{j\pi(f/f_s)N}}e^{-j\pi(f/f_s)L}, \quad -\frac{f_s}{2} \le f \le \frac{f_s}{2}, \quad \text{EQUATION 5}$$

where L represents a number of taps in the FIR filter. The objective is to derive an L tap FIR filter whose spectrum is the inverse of that in EQUATION 4. The factor $e^{j\pi(f/f_s)N}$ removes a linear phase resulting from a time delay of N/2 in EQUATION 1. The factor $e^{-j\pi(f/f_s)L}$ generates a phase on the filter that corresponds to a delay of L/2 samples. EQUATION 4 is invertible since the spectrum of the Barker code contains no zeros.

The spectrum is evaluated for M frequency points (M≥L) in the range $$\left[-\frac{f_s}{2}, \frac{f_s}{2}\right]$$

to form a vector D as shown in EQUATION 6:

$$D = (D(f_0)D(f_1) \ldots D(f_{M-1}))^T \quad \text{EQUATION 6}$$

where T represents the transpose.

An L tap FIR filter that minimizes an error between a calculated spectrum and a desired spectrum, in a least squares sense, is given by a minimization function shown in EQUATION 7:

$$\hat{h} = \underset{h}{\operatorname{argmin}} \|\omega h - D\|^2, \quad \text{EQUATION 7}$$

where h can be represented as shown in EQUATION 8:

$$h = (h(0)h(1) \ldots h(L-1)), \quad \text{EQUATION 8}$$

and ω is an M×L Fourier matrix with elements defined as shown in EQUATION 9:

$$\omega_{ml} = e^{-j2\pi(lm/M)}, \quad \begin{array}{l} l = 0, \ldots, L-1 \\ m = 0, \ldots, M-1 \end{array}. \quad \text{EQUATION 9}$$

A solution of EQUATION 7 is shown in EQUATION 10:

$$\hat{h} = (\omega^H \omega)^{-1} \omega^H D, \quad \text{EQUATION 10}$$

where H represents a complex conjugate transpose. Where the orthogonality condition is satisfied, $\omega^H \omega$ can be denoted as shown in EQUATION 11:

$$\omega^H \omega = MI, \quad \text{EQUATION 11}$$

where I is an identity matrix. EQUATION 10 can be reduced as shown in EQUATION 12:

$$\hat{h} = \frac{1}{M} \omega^H D. \quad \text{EQUATION 12}$$

A sample from $\hat{h}$ can be determined as shown in EQUATION 13:

$$\hat{h}(l) = \frac{1}{M} \sum_{m=0}^{M-1} D(f_m) e^{j2\pi\left(\frac{lm}{M}\right)}. \quad \text{EQUATION 13}$$

In other words, an optimal FIR filter, in the least squares sense, is an inverse discrete Fourier transform of a sampled desired frequency spectrum of the filter. This can be interpreted as taking the L first samples of the inverse FFT of the sampled desired spectrum.

The decoder 120, for final decoding, computes a convolution of a time-reversed signal and a decreased bit-rate version of h(n) as shown in EQUATION 14:

$$g(n) = \sum_{l=0}^{L-1} h(l)p(-n + l \cdot Tf_s), \quad \text{EQUATION 14}$$

where g(n) is the recovered signal at sample time n.

Figure 5:
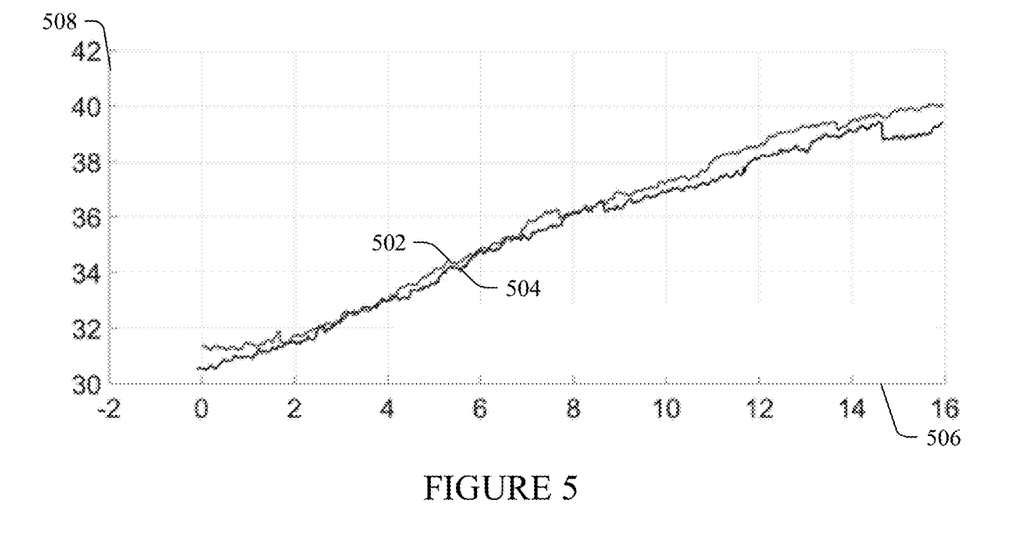
FIG. 5 shows plots of temperatures of a surface of a transducer array with the coded excitation signal and with the sinusoidal excitation signal.
Figure 6:
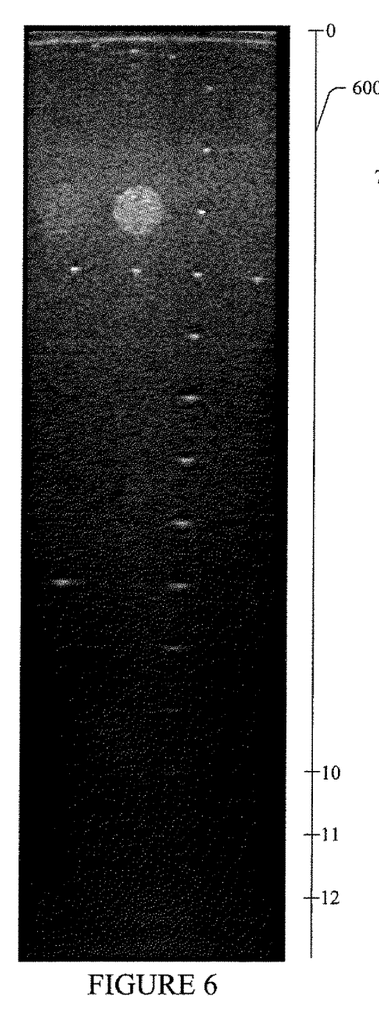
FIG. 6 shows an ultrasound image acquired with the sinusoidal excitation signal and a penetration depth thereof.
Figure 7:
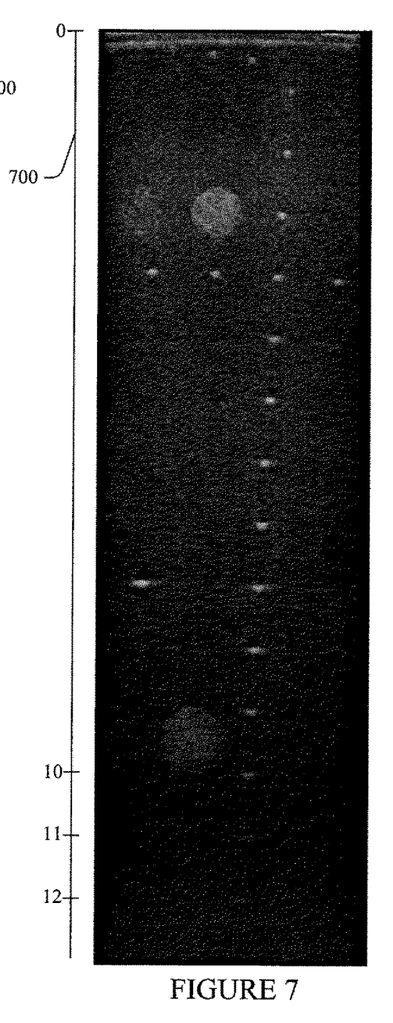
FIG. 7 shows an image acquired with the coded excitation signal and a penetration depth thereof.

FIG. 5 shows a comparison of a temperature at a front surface of the array 102 for a 1.5 cycle sinusoidal excitation signal (a plot 502) and a 7-bit Barker coded excitation signal (a plot 504) described herein. A first (x) axis 506 represents time duration (e.g., in minutes), and a second (y) axis 508 represents temperature. From FIG. 5, the temperature is about the same in both cases. Raising the excitation length (e.g., from 1.5 to 7 cycles) also does not raise the temperature, unlike with PZT elements. FIGS. 6 and 7 show examples images using the 1.5 cycle sinusoidal excitation signal and the 7-bit Barker coded excitation signal. A legend 600 represents depth (e.g., in centimeters, cm). From FIGS. 6 and 7, a penetration depth using the Barker coded excitation signal is greater than a penetration depth using sinusoidal excitation signal. From FIGS. 5-7, the coded excitation described herein increases penetration depth without introducing significantly more heat.

The increase in penetration depth can be mathematically quantified. A non-limiting example is provided next. The RF echoes are attenuated by the tissues scanned. For a tissue with attenuation of 0.5 dB/cm×MHz, the acoustic wave would be attenuated 2×10×4.1×0.5=41 dB for a received signal using a 4.1 MHz transducer with an imaging depth of 10 cm. In this example, $2 \times d \times fc \times \alpha$ is the total attenuation in the signal in which d is the imaging depth in cm, fc is the transducer center frequency in MHz, $\alpha$ is the attenuation coefficient of the tissue in dB/cm×MHz), and the coefficient 2 is because the sound penetrates the tissue twice. For the same transducer and the same tissue, an improvement of 10.25 dB using the coded imaging is achievable. This improvement translates to 10.25/(0.5*2*4.1)=2.5 cm improvement in imaging depth.

The example above describes an example using the 7-bit Barker code +1 +1 +1 −1 −1 +1 −1. The other Barker codes can alternatively be utilized. The coding schemes for these respectively are: +1 −1 or +1 +1 (2-bit), +1 +1 −1 (3-bit), +1 +1 −1 +1 or +1 +1 +1 −1 (4-bit), +1 +1 +1 −1 +1 (5-bit), +1 +1 +1 −1 −1 −1 +1 −1 −1 +1 −1 (11-bit), and +1 +1 +1 +1 +1 −1 −1 +1 +1 −1 +1 −1 +1 (13-bit). Other binary coding schemes without any zeros can also be used. The particular code used for a particular scan can be preprogrammed into the available protocols. Generally, a longer code is better-suited for deeper depths and higher frequency imaging, and a shorter code is better-suited for shallower depths and lower frequency imaging.

For example, in one instance a 5 MHz scan protocol includes the 7-bit Barker code, an 8 MHz scan protocol includes an 8-bit code, a 12 MHz scan protocol includes the sinusoidal signal without any coding, etc. It is to be understood that the above example is not limiting. For example, in another instance the 12 MHz scan uses coded (Barker or other) excitation. In general, when a sonographer switches between imaging frequencies at the imaging system 100, the code is automatically switched and is dependent on the frequency as specified in the corresponding scan protocols. In one instance, this allows a same transducer array (e.g., a single wide bandwidth transducer array such as a 5-12 MHz transducer array) to be used for multiple different imaging, including both superficial and deep imaging, alternatively, during a same or different examination of a subject(s).

Generally, CMUTs are fabricated using standard micro-machining processes that provide all the advantages of the integrated circuit technology, such as ease of fabrication, mass production, and repeatability. The large bandwidth also makes the CMUT well-suited for nonlinear imaging where pressure is transmitted at the fundamental frequency and higher order harmonics are received. The coding approach described herein enables adaptive and frequency multi-band imaging using CMUTs. This ensures the use of wide temporal bandwidth, and produces very good axial resolution and allows different imaging modalities by using only a single CMUT transducer (Low frequency and high frequency imaging).

Figure 8:
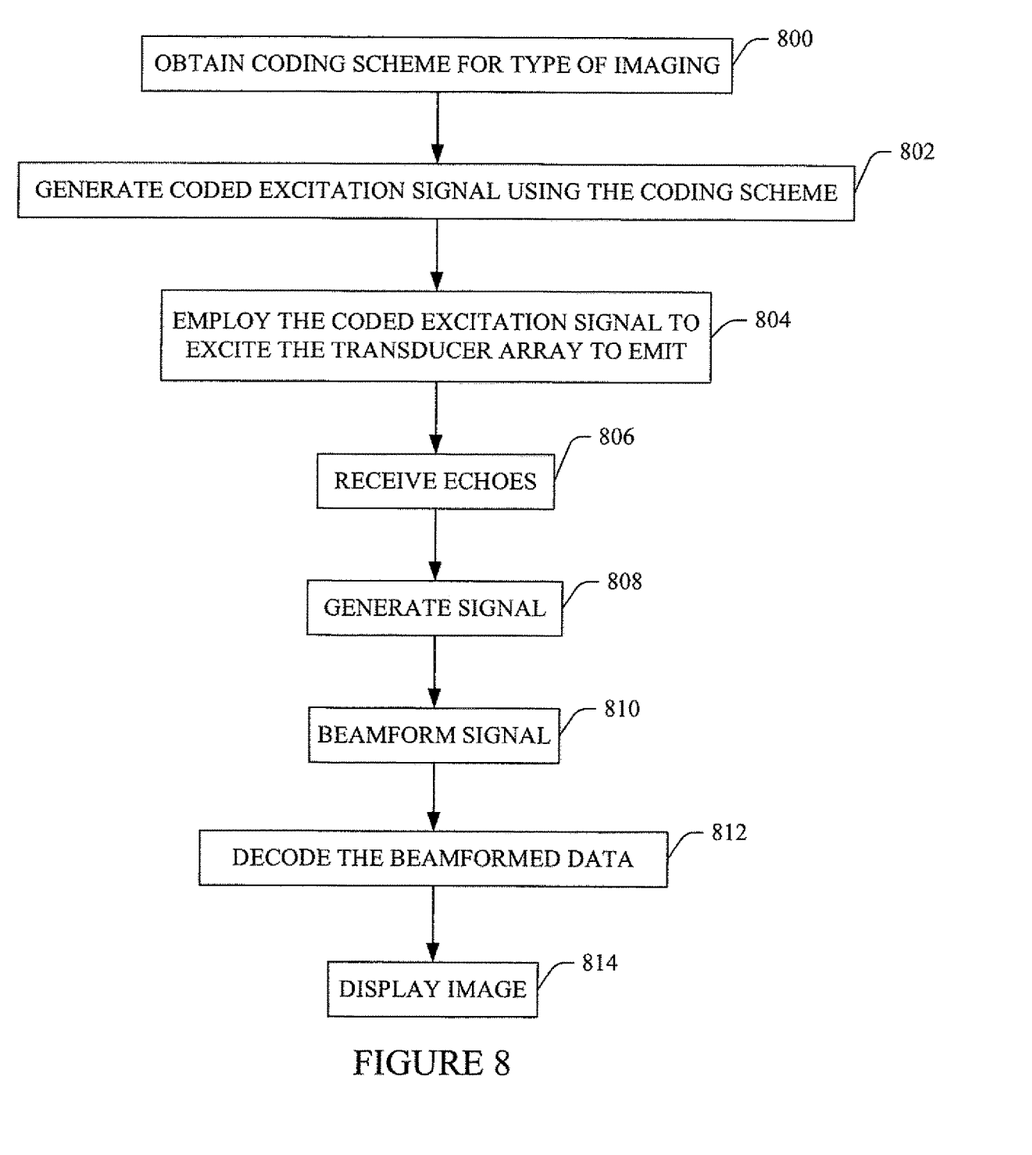
FIG. 8 illustrates a method in accordance with an embodiment(s) described herein.

FIG. 8 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 800, a coding scheme is obtained for a type of imaging of an examination, as disclosed herein. For example, the coding is selected based on the transducer frequency being utilized.

At 802, a coded excitation signal is generated based on the coding scheme, as disclosed herein.

At 804, the coded excitation signal is employed to excite a transducer array to emit an ultrasound signal, as disclosed herein.

At 806, echoes produced in response to the ultrasound signal are received;

At 808, a signal indicative thereof is generated, as disclosed herein.

At 810, the signal is beamformed producing beamformed data, as disclosed herein.

At 812, the beamformed data is decoded to remove the coding, as disclosed herein.

At 814, an ultrasound image is displayed.

Optionally, a different frequency is selected for another scan during the imaging examination, where a different coding scheme for the newly selected frequency is obtained, and acts 804-814 are repeated.

The embodiments described herein can be implemented via one or more computer processors (e.g., a micro-processor, a central processing unit (cpu), etc.) executing one or more computer readable instructions encoded or embodied on computer readable storage medium (which excludes transitory medium) such as physical memory, which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An imaging system, comprising:
   transmit circuitry including:
      a signal generator; and
      at least one excitation coding scheme, wherein the transmit circuitry combines an excitation signal generated by the signal generator with an excitation coding scheme of the at least one excitation coding scheme to produce a coded excitation signal;
   a transducer array with an array of capacitive micromachined ultrasonic transducer elements,
   wherein the array of capacitive micromachined ultrasonic transducer elements is excited with the coded excitation signal to emit ultrasound signals and using the coding scheme does not introduce heating on the capacitive micromachined ultrasonic transducer elements, and wherein the array of capacitive micromachined ultrasonic transducer elements receives echo signals produced in response to the ultrasound signals interacting with structure and generates electrical signals indicative thereof;
   a beamformer that beamforms the electrical signals;
   a decoder that removes the coding from the beamformed signals; and
   a display that displays an image with the decoded signals.

2. The imaging system of claim 1, wherein the excitation signal is a sinusoidal signal and the excitation coding scheme is a binary coding signal with a plurality of values, wherein no value of the plurality of values equals zero, and the coded excitation signal is a sinusoidal signal.

3. The imaging system of claim 2, wherein the transmit circuitry combines the excitation signal and the excitation coding scheme by convolving the sinusoidal signal and the binary coding scheme.

4. The imaging system of claim 2, wherein the excitation coding scheme is a Barker code.

5. The imaging system of claim 1, wherein the decoder compresses the excitation coding scheme and removes the excitation coding scheme from the beamformed signals with the compressed excitation coding scheme.

6. The imaging system of claim 5, wherein the decoder applies a finite impulse response filter to compress the excitation coding scheme.

7. The imaging system of claim 6, wherein the finite impulse response filter approximates an inverse filter of the excitation coding scheme.

8. The imaging system of claim 7, wherein the decoder convolves a time reversed excitation signal and a decreased bit-rate version of the coding scheme.

9. The imaging system of claim 1, wherein the coding scheme increases a penetration depth of the ultrasound signals.

10. The imaging system of claim 1, wherein using the coding scheme does not increase a temperature of the transducer array.

11. A method, comprising:
generating a coded excitation signal using coding scheme that does not introduce heating on capacitive micromachined ultrasonic transducer elements;
exciting a transducer array to emit an ultrasound signal with the coded excitation signal, wherein the transducer array includes an array of the capacitive micromachined ultrasonic transducer elements;
receiving signals indicative of echoes received by the transducer array, wherein the echoes are produced in response to the ultrasound signal with the coded excitation signal interacting with structure;
beamforming the signals;
decoding the beamformed signals; and
visually presenting an image with the decoded signals.

12. The method of claim 11, further comprising:
generating the coded excitation signal with an excitation signal and a first binary coding scheme, which includes a plurality of values, none equal to zero, in response to an input indicating a first scan with a first frequency, wherein the coded excitation signal includes peaks between positive one and negative one, peaks between zero and negative one, and peaks between positive one and zero.

13. The method of claim 12, further comprising:
generating a different coded excitation signal with the excitation signal and a second binary coding scheme, which includes a plurality of values, none equal to zero, in response to a different input indicating a different scan with a different frequency; and
exiting the same transducer array with the different coded excitation signal.

14. The method of claim 12, wherein the excitation signal is a sinusoidal signal and generating the coded excitation signal includes convolving the sinusoidal signal and the binary coding scheme.

15. The method of claim 14, wherein the excitation coding scheme is from a group consisting of a 2-bit Barker code; a 3-bit Barker code; a 4-bit Barker code; a 5-bit Barker code; a 7-bit Barker code; an 11-bit Barker code and a 13-bit Barker code.

16. The method of claim 12, wherein decoding the beamformed signals includes convolving a time reversed version of the excitation signal and an inverse of the code.

17. The method of claim 11, wherein the coding scheme increases a penetration depth of the ultrasound signals.

18. The method of claim 17, wherein using the coding scheme does not increase a temperature of the transducer array.

19. A non-transitory computer readable medium encoded with computer executable instructions which when executed by a processor cause the processor to:
generate a coded excitation signal with a coding scheme;
excite a transducer array to emit an ultrasound signal with the coded excitation signal, wherein using the coding scheme does not add heat to a surface of the transducer array, and the transducer array includes an array of capacitive micromachined ultrasonic transducer elements;
beamform echo signals received by the transducer array;
extract a signal from the beamformed signals; and
display an image with the extracted signal.

20. The non-transitory computer readable medium of claim 19, wherein using the coding scheme increases a penetration depth of the ultrasound signals and does not increase a temperature of the transducer array.

* * * * *